United States Patent [19]

Vojcek et al.

[11] Patent Number: 5,994,411
[45] Date of Patent: Nov. 30, 1999

[54] FORMULATED PRODUCT FOR EMBRYONIC RETARDATION OR DISCORDANCE

[75] Inventors: László Vojcek; Tibor Bedö; Tibor Pók; Gábor Bartók; Zsolt Ágni, all of Debrecen, Hungary

[73] Assignee: Biogal Gyogyszergyar RT, Debrechen, Hungary

[21] Appl. No.: 09/117,830

[22] PCT Filed: Dec. 30, 1997

[86] PCT No.: PCT/HU97/00090

§ 371 Date: Nov. 13, 1998

§ 102(e) Date: Nov. 13, 1998

[87] PCT Pub. No.: WO98/29103

PCT Pub. Date: Jul. 9, 1998

[30] Foreign Application Priority Data

Dec. 30, 1996 [HU] Hungary .................................. 96 03631

[51] Int. Cl.$^6$ ...................................................... A61K 31/10
[52] U.S. Cl. ................................................................ 514/709
[58] Field of Search ............................................... 514/709

[56] References Cited

U.S. PATENT DOCUMENTS 3,509,207  4/1970  Esteve-Subirana ..................... 260/512

OTHER PUBLICATIONS

Embase Abstract No. 97179584.
Ghiglione et al., Treatment of nonproliferative diabetic retinopathy with a peptide fraction, Drug investigation, (1992) 4/1 pp. (1–6) May 1992.

*Primary Examiner*—Keith D. MacMillan
*Assistant Examiner*—Vickie Kim
*Attorney, Agent, or Firm*—Smith, Gambrell & Russell; Beveridge, DeGrandi, Weilacher & Young

[57] ABSTRACT

Subject of the invention is a molecule characterized by the general structure as no. 1., where meaning of x: 1 or 2 valency metallic ion adequate from therapeutic point of view, value of n: 1 or 2, or the application of its metabolite being suitable for the treatment or prevention of embryonic retardation or discordance.

9 Claims, 1 Drawing Sheet

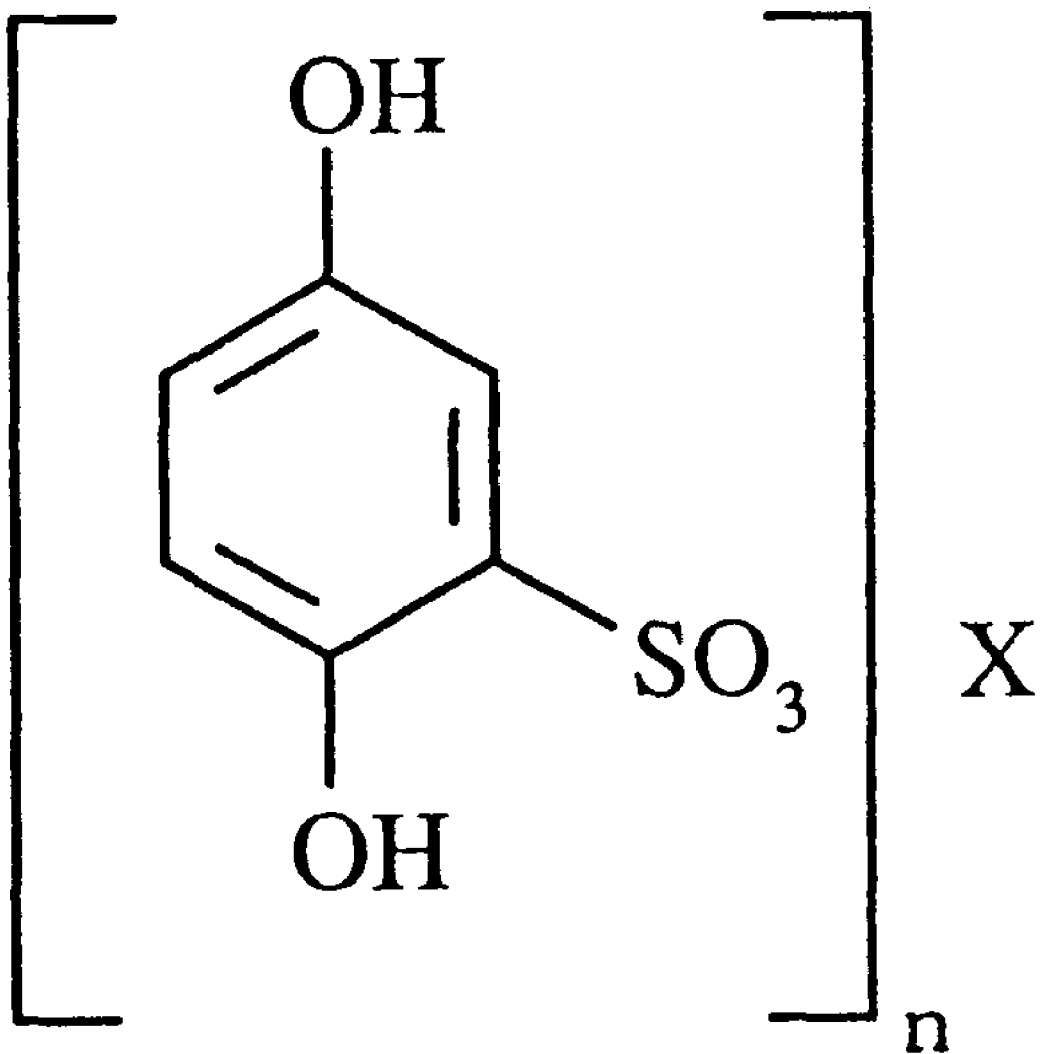
Structure No. 1.

FORMULATED PRODUCT FOR EMBRYONIC RETARDATION OR DISCORDANCE

The application, 371 of PCT/HU97/00090 (filed on Dec. 30, 1997), has priority of foreign application Hungary P 96 03631, filed on Dec. 30, 1996.

FORMULATED PRODUCT

Subject of the invention is a molecule characterised by the general structure as no. I., where meaning of x: 1 or 2 valency metallic ion adequate from therapeutic point of view, value of n: 1 or 2, or its metabolite witch is used the for the treatment or prevention of embryonic retardation or discordance.

The application of the formulated product containing calcium dobesilate as an active ingredient in the human therapy from the 1970's has been known in several indication area.

The active constituent is applied in several formulated forms, among which the most important products are the oral products (tablet, capsule) and which are known after their widespread registered name as Doxium manufactured by e.g. the OB Lab. (Switzerland).

The manufacture of the calcium dobesilate (calcium salt of 2,5-dihydroxybenzene sulphonic acid) is discussed in the U.S. Pat. No. 3,509,207 and ES 335945 patents.

Major indication areas and experiences are reviewed as follows.

The examination of 120 patients suffered in venous dilatation (primer and secunder varicosity) were done by Pietrek, G. (Z. Allg. Med. 56./1980/1217–1222) after 3 months long oral Doxium treatment. According to his experience the complaint of the patients decreased (parachroma, oedema, excess weight sensation).

The treatment of patients suffered in chronic venous insufficiency by double-blind examination was reported by Haachen, H. J. and Lorenz, P. (Angiology 1982. July 33 (7) 480–488). As a result of the treatment with Doxium the subjective complaint of the patients significantly decreased and their health improved according to the plethysmographic analysis too.

Patients suffered in the above illnesses were examined by Balmer, A. (Schweiz. Rundscbau für Med. Praxis, 67 (39) 1978, 1440–1443) before and after the external treatment with Doxivenil gel. This product contains 2% calcium dobesilate and 2% heparinoid (potassium hydrodextran sulphate). Patients tolerated the treatment very good, and the health condition of 80–87% of them turned to favourable.

Three months long treatment of patients for diagnosed retinopathy deabetica with oral Doxium was published Barras, J. P. and Graf, C (VASA/1980/9(2)161–164). According to three different analytical methods at the end of their experiment the viscosity of both the plasma and the whole blood reduced. The relative viscosity and the hematocrit value remained unchanged.

The capillary permeability of diabetic patients were examined by Sevin, R. and Cuendet, J. F. (Ophtalmologica 162:33–40/1971/33–40). Retinopathic patients were divided into the following four groups:

exclusively microaneurysm,
few retinal haemorrhage,
considerable retinal haemorrhage,
extraretinal haemorrhage.

According to the results of the fluorescein angiographic analysis the oral dosage of Doxium has a favourable effect on the pathological permeability of the capillaries, and the capillary resistance values.

Treatment of pile haemorrhage with Doxiproct suppository (containing 250 mg calcium dobesilate and 40 mg lidocain active constituent) was published by Berson, I. (Schweizerische Rundschau für Med. Praxis (1975.03.11./ 64 (10) 299–301). As a result of dosing two times per day for two weeks, improvement was detected 87% of the cases.

Summarising the literature data it can be concluded, that the known indications for the oral application of the calcium dobesilate are the followings: microangiopathy; particularly retinopathy deabetica; chronic venous insufficiency; primer varicosity; pregnancy varicosity; leg ulcer; night sural spasm; ankle oedema. On the basis of the data being available at present, it is applicable as an adjuvant in the following cases: external thrombophlebitis; postthrombotic syndrome; oedema; stasis dermatosis; piles complaint.

According to the literature data relating to the way of action, the calcium dobesilate effects via the regulation of the pathological capillaric wall functions (increased permeability and reduced resistancy). It inhibits the decomposition of the collagen fibres, reduces the hyperviscosity of both the plasma and the blood. Indirectly it inhibits the lymph flow, and as a consequence of this reduces the oedema. Maximum blood concentration value can be reached 6 hours after the oral dosing of 500 mg calcium dobesilate, which is about as high as 8 $\mu$g/ml. Between 3 and 10 hours a platform can be experienced. After 24 hours dosing its blood concentration is 3 $\mu$g/ml. As an average the half-period of plasma is 5 hours. Calcium dobesilate is connected to the plasma peptide by its 20–25% rate. It can not be transferred through the barrier between the brain and the blood and not even through the placenta barrier. It can be detected in small quantity in the mother's milk. In the first 24 hours about 50% of the orally dosed quantity is secreted with the urine, and very similar to this value is its secretion with the faeces. Major quantity of the compound is eliminated without its any transformation.

Independently from the period of the treatment, the compound is well tolerable. Its toxicity is very low, the $LD_{50}$ value tested with mousses is 700 mg/kg. According to the literature data known up to the present there is not any medicine interaction.

According to our knowledge the application of the calcium dobesilate during the pregnancy—except the treatment of varicosity has not been raised yet. Probably its reason is, that the informing bulletin about the oral formulated product (Doxium, producer e.g. OM Lab. Switzerland) contains the following statements, as: It is not recommended during the first three months of the pregnancy." "In case of pregnancy the medical attendant should be informed." "Medicine does not get across the barrier of the placenta."

During the pregnancy several clinical picture can be formed, one of them of which is the embryonic retardation. It means, that the development inside the uterus is retarded compering it to the average development ratio in given pregnancy phase. According to the domestic and international statistical data the frequency of the embryonic retardation is within 10–30%. Large fluctuation refers to the fact, that the demand for the detection and the instrumental conditions were established only in the past 5–10 years. Babies who are born with 2500 g birth weight nowadays belong not to the retarded new-born infant but to the premature birth, especially if the birth happened before the 37th pregnancy week. In the case of the new-born infants who are born after this period and exceeding the 2500 g birth weight, the diagnosis and the fact of the retardation is established only in such institutes, where a neonatalogist specialist is at present during the birth, or the new-born infant needs intensive therapy. For this reason the statistical data may be more favourable, then the real incidence rate.

Additional problem is, that the complication of the illness very often leads to the intrauterine necrosis and furthermore the prenatal mortality rate and the incidence rate of the further damages are very high.

According to the literature data published till now the development of the illness may be resulted by certain predisposing maternal factors, such as smoking, alcoholism, malnutrition, metabolic and endocrine illnesses, chronic kidney, liver, lung illnesses, gravid toxaemia, pre-eclampsia. Placenta also could be a possible source, e.g. disorders in the uterus development, insertion difficulties of the placenta, its early ageing, or the discordance twin pregnancy. However these factors have not been examined completely, since beside congenital uterus disorder and after retarded pregnancy even a normal pregnancy can be developed.

There are two classical form of the intrauterine retardation:

retardation is from the early stage of the pregnancy as called "primary retardation", or after a normal initial development, in the second or the third period of the pregnancy the development of the embryo become retarded or stopped. This is the "secondary retardation".

Setting up of the diagnosis was made possible by the spreading of the modern ultrasonographic technics.

According to the recommendation of the European (and the Hungarian) Ultrasound Association the examination of the following five parameters are necessary and sufficient to decide in a case about the embryonic retardation:

diameter of the embryonic temporal bone, circumference of the embryonic skull, circumference of the embryonic chest, diameter of the embryonic chest, length of embryonic femur.

By the application of the Colour Doppler ultrasonographic technic even certain circulatory measurements can be done too, which back the setting up of the diagnosis. As a result of these data recent years it become evident, that the haematocrit values of the retarded embryos are high, and the carbohydrate and lipid reserves were consumed. In the placenta of the retarded embryos multifocal thrombotization and early necrosis were experienced, which led to the prematurity of the placenta.

Efforts were made from the 1950's for the treatment of the embryonic retardation. Trials were made to increase the maternal carbohydrate level, or parallel with this the low dosing of insulin, Diaphyllin dosing in order to increase the maternal circulation, application of vacuum chamber placed on the maternal abdominal wall in order to reduce the atmospheric pressure, or the application of salicylate containing medicines in order to reduce the maternal blood viscosity (or aggregation). Among the latter ones the dosing of acetyl salicylate was examined and published by Shen J. at al. (Br.J.Clin.Pharmacol. 35., 1993., No.6. 664–67), who dose the medicine to those pregnants, who were endangered by pregnancy convulsions (preeclampsia) and retarded embryonic development. It was established, that in each examined cases the acetyl salicylate gets into the embryo, and there is not any significant difference between the maternal and embryonic blood concentrations. There was not any effect reported in connection with the embryonic retardation. Uterus artery was examined with Doppler ultrasonographic method in the above prognosed clinical pattern by S. Campbell (The Sixth World Congress of Ultrasound in Obstetrics and Gynecology; Rotterdam, Oct. 27–31, 1996. Book of Abstracts p. 256, article no. 517). There was not any result reported in connection with the embryonic retardation in the case of prophylactic Aspirin dosing. These are in harmony with the fact—known by the experts—, that none of the above listed treatments resulted the onset of the increase in weight of the retarded embryo, thus the application of none of them were spreaded.

As a summary of the above it can be concluded, that the predisposing factors of the illness are known, prognosis of the formation is partly dissolved, but the efficiency of the therapeutic methods is very poor.

Concentrating on the curing during the research work our target was to accomplish a medical treatment, which is suitable for the treatment of a retarded embryo, the prevention of the prognosed retarded embryo, in the case of a discordance (multiple pregnancy with different development rate) to improve the condition of the retarded embryo.

During the experiments unexpectedly we recognised, that the calcium dobesilate is suitable for the above treatment although it does not get through the barrier of the placenta, and directly it can not be detected in the embryo. On the contrary of the previous medical treatment this is surprising, since the scientists search for such products, which is able to influence the state of the embryo directly by their presence. This recognition is even surprising considering other directions of the research work, where the increase of the maternal "offer side" was considered as primary importance by realising this conception administering subsequently carbohydrate or glucose into the organism of the pregnant. However these attempts did not give results.

Accordingly the subject of the invention is a molecule characterised by the general structure as no. I., where meaning of x: 1 or 2 valency metallic ion adequate from therapeutic point of view, value of n: 1 or 2, or the application of its metabolite being suitable for the treatment or prevention of embryonic retardation and for the treatment or prevention of discordance. The chemical structure of the molecule is presented in the 1st picture.

Additional subject of the invention is the application of the calcium dobesilate for the treatment or prevention of embryonic retardation and for the treatment or prevention of discordance.

Accordingly the above active constituent is suitable for the treatment of the developed embryonic retardation in its early stage or the prevention of it. Predisposing factors were discussed previously, consequently in the case of their earlier accumulated occurrence the development of the illness is more probable. If in the foregoing pregnancies retardation happened only in one case, presuming the development of a further retardation is not rightful. However after two or more retarded new-born infants, in the case of a further pregnancy in all probability the clinical picture will be developed again.

According to a presumable mechanism under the influence of the active constituent the blood supply of the placenta on the maternal and the embryonal border is increased, and consequently the oxygen and nutrient supply towards the embryonic side is intensified. In the area of the villus of the placenta the blood congestion and the formation of the microthrombus comes to an end. Although the maternal and embryonal blood vessels do not mix, by the improvement of the maternal blood volume and blood pressure the flow of blood volume and blood pressure towards the embryo is intensified too.

According to our experiences in the case of discordance the dosing of the active constituent has a favourable effect on the development of the gemini-B or -C being retarded in the development before. According to a presumable mechanism the positive result is due to the improvement of the oxygen and nutrient supply in the placenta, which provide the development of the gemini-B or -C.

This mechanism is not connected with the mechanism of the formal indications, this can not be concluded from them. This is supported by the fact, that after the examination of the patients suffered in pre-eclampsia (which accompanying is: maternal oedema, albuminuria and high blood pressure) the authors declared, that the calcium dobesilate did not decrease the maternal albuminuria and the hypertension, moreover the transformation of the blood platelets was favourable. In the above clinical picture (see huge amount of studies) the change in the embroil retardation being necessarily at present was not stated or considered (Lege Artis Medicine Apr. 07, 1994 page 902–910).

In order to support the application on the new indication area the test of the calcium dobesilate was made with pregnants divided into three groups. In the case of the patients belonged to the 1st group embryonal retardation was diagnosed by ultrasound analytical method according to the measurements mentioned before as diameter of the embryonic temporal bone, circumference of the embryonic skull, circumference of the embryonic chest, diameter of the embryonic chest, length of embryonic femur and by embryonal cardiovascular examinations, i.e.:

analysis of the area "below the phonic graph" of artery blood flow of the umbilical cord and supplying the resistance index of the same artery;

measurement the conditions of the downflow branch of the embryonic aorta;

analysis of the area "below the phonic graph" of embryonal artery cerebri media blood flow and supplying the resistance index of the same artery (these analysis were applied from the 28th week of the pregnancy).

Patients belonged to the 2nd group were discordance twin pregnants, and the diagnosis were devised according to the above written methods.

In the case of the patients belonged to the 3rd group, because of the accumulated occurrence of predisposing factors embryonal retardation could be expected. In this group both normal and twin pregnancies took place.

1st Group—Diagnosed Embyonal Retardation

According to the diagnosis obtained after the above written analysises 144 pregnants belonged to this group. Patients received daily 3×1 Doxium capsules (500 mg calcium dobesilate per capsule).

The minimal treatment period was two weeks, the optimal 6–10 weeks.

Treatments were started in the 2–3 third period of the pregnancy. Beside the above written embryonal analysis and the determination of the cardiovascular conditions after the introduction of the therapy the quantity of the amniotic fluid was measured in weekly frequency and also the maturity degree of the placenta was determined. Based on the above parameters if the degree of the embryonal development and the value of the embroil weight reached the characteristic value of a pregnancy age, we started the maintenance treatment. The maintenance dose was daily 2×1 Doxium capsules.

According to our results based on both the embryonal stature and the functional analysis (non-stress-test, cardiovascular parameters) the bearing of the pregnancy become possible in those cases, when beside the retardation the functional state of the embryo was the reason for termination of the pregnancy. The effect of Doxium was the most expressed in cases and resulted in mature weight or new-born infant weight in the range of 10–90 percent—good for bearing till the term or nearly till the term, if the treatment started before the 32nd to 34th gestation week and the embryonal retardation did not associate with the illness of the maternal organism and/or embroil retardation in the development and/or dry labour.

2nd Group—Discordance Embryonal Twin Pregnancy

In this group 23 pregnants were examined. Diagnosis and the control of the patients were done as it was written in the 1st group.

Initial dose was daily 3×2 Doxium tablets (250 mg calcium dobesilate per capsule). The maintenance dose was daily 2×2 Doxium tablets.

Our results were as good as was written also in the case of the 1st group. In both groups the new-born infants were not haemoconcentrated;

rising of the thrombocyte aggregation was not characterisitc;

viscosity of blood van normal;

saturation of the oxygen was physiological;

carbohydrate; lipid and peptide metabolism did not need any correction in cases, when the treatment lasted only 8–10 weeks.

3rd Group—Prognosed Embryonal Retardation

For this examination 93 pregnants were selected in which cases the accumulated occurrence of predisposing factors were found. The control of the patients were done as it was written in the 1st group. Dose of Doxium (daily 2×2 Doxium tablets, the same as written before for the maintenance dose) was started in the 14th week of the pregnancy, and was given up 2 weeks before the termination of the birth.

According to our experiences embryonal retardation was not found in the examined circle.

As a Summary of our Results calcium dobesilate is efficiently applicable for the treatment or the prevention of the above illnesses;

on the basis of the treated group the contraindication of illness did not become known;

any medicine interaction was not experienced in the cases of the treated patients.

If the dosing period is not more then 2 weeks, the recommended minimal daily calcium dobesilicate dosis is 500 mg and the maximal is 3000 mg.

Advantages of the Solution According to the Patent the application of an active constituent is recommended to a new indication area, which human use has already been tested for more then 20 years;

formulated products do not have any or have only very limited side effect;

the active constituent is not able to get over the placenta, it does not load the organism of the embryo;

it provides good therapeutic results in those areas, where till now the treatment had only limited success;

during the 2nd or 3rd third of the pregnancy it is enough to start the dosing of the medicine even only for prevention.

We claim:

1. A method of treating and embryonic retardation or discordance, comprising:

administering to a patient in need thereof, an effective amount of a compound having the following formula:

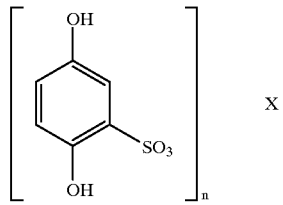

wherein X is a metallic ion having a valence of 1 or 2; and the value of n is either 1 or 2.

2. A method of treating and embryonic retardation or discordance, comprising:

administering to a patient in need thereof, an effective amount of a compound having the following formula:

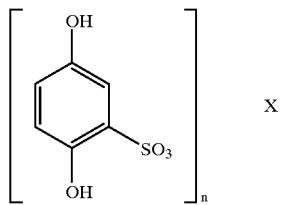

wherein X is calcium; and the value of n is 2.

3. A method of treating and embryonic retardation or discordance, comprising:

administering to a patient in need thereof, an effective amount of calcium dobesilate.

4. The method according to claim 1, wherein said method is for the treatment of embryonic retardation.

5. The method according to claim 1, wherein said method is for the treatment of discordance.

6. The method according to claim 2, wherein said method is for the treatment of embryonic retardation.

7. The method according to claim 2, wherein said method is for the treatment of discordance.

8. The method according to claim 3, wherein said method is for the treatment of embryonic retardation.

9. The method according to claim 3, wherein said method is for the treatment of discordance.

* * * * *

UNITED STATES PATENT AND TRADEMARK OFFICE
CERTIFICATE OF CORRECTION

PATENT NO. : 5,994,411
DATED : November 30, 1999
INVENTOR(S) : Vojcek et al.

It is certified that error appears in the above-indentified patent and that said Letters Patent is hereby corrected as shown below:

IN THE CLAIMS:

In claim 1, line 1 (column 7, line 2), after "treating" delete "and".

In claim 2, line 1 (column 7, line 24), after "treating" delete "and".

In claim 3, line 1 (column 8, line 12), after "treating" delete "and".

Signed and Sealed this

Thirteenth Day of March, 2001

Attest:

NICHOLAS P. GODICI

Attesting Officer         Acting Director of the United States Patent and Trademark Office